United States Patent [19]

Kujath et al.

[11] Patent Number: 5,079,244
[45] Date of Patent: Jan. 7, 1992

[54] SUBSTITUTED 3-AMINOSYDNONE IMINES, PHARMACEUTICAL COMPOSITIONS CONTAINING SAME, AND PROCESS FOR ADMINISTERING SAME

[75] Inventors: Eckard Kujath, Maintal; Christian Baumgartner, Stuttgart; Karl Schöafinger, Alzenau; Rudi Beyerle, Frankfurt; Melitta Just, Nidderau; Helmut Bohn, Schöneck; Jörg Ostrowski, Rodenbach, all of Fed. Rep. of Germany

[73] Assignee: Cassella Aktiengesellschaft, Frankfurt, Fed. Rep. of Germany

[21] Appl. No.: 534,152

[22] Filed: Jun. 7, 1990

[30] Foreign Application Priority Data

Jun. 30, 1989 [DE] Fed. Rep. of Germany ....... 3921460

[51] Int. Cl.$^5$ .................. A61K 31/395; C07D 413/04
[52] U.S. Cl. .................. 514/227.8; 514/326; 514/236.2; 514/252; 514/364; 544/138; 544/60; 544/367; 548/125
[58] Field of Search ............... 546/209, 289; 514/326, 514/227.8, 236.2, 252, 364; 544/138, 60, 367; 548/125

[56] References Cited

U.S. PATENT DOCUMENTS 4,888,333  12/1989  Bonn et al. .......................... 546/209
4,937,244   6/1990  Schönafinger et al. ............. 546/209

Primary Examiner—Robert T. Bond
Attorney, Agent, or Firm—Perman & Green

[57] ABSTRACT

Substituted 3-aminosydnone imines of the general formula I

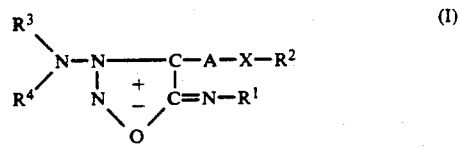

and their pharmacologically acceptable acid addition salts, in which
A denotes an alkylene chain;
X denotes one of the groups —O— or —S—;
$R^1$ denotes e.g. hydrogen;
$R^2$ denotes e.g. an alkyl group,
are prepared by cyclization of a compound of the formula II

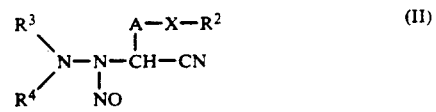

and, if appropriate, subsequent acylation, and have useful pharmacological properties.

10 Claims, No Drawings

SUBSTITUTED 3-AMINOSYDNONE IMINES, PHARMACEUTICAL COMPOSITIONS CONTAINING SAME, AND PROCESS FOR ADMINISTERING SAME

BACKGROUND OF THE INVENTION

1. Field of the Invention

The present invention relates to novel N-substituted sydnone imines, and to novel N-substituted amino acetonitriles for producing such sydnone imines, and to processes for the preparation of such compounds. The invention also relates to pharmaceutical compositions containing the present sydnone imine or acetonitrile compounds, and to the preparation and use of such compositions for the control or prophylaxis of disorders of the cardiovascular system, including angina pectoris, functioning as antihypertensive medicaments, for example.

2. Description of the Art

The novel compounds and compositions of the present invention have been found to have considerably prolonged duration of action and potency as compared to known 3-amino sydnone imines such as molsidomine and as compared to other sydnone imines which are also substituted in the 4-position.

SUMMARY OF THE INVENTION

The invention relates to pharmacologically active substituted 3-aminosydnone imines of the general formula I

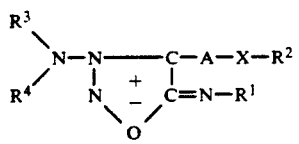

and their pharmacologically acceptable acid addition salts, in which

A denotes a straight-chain or branched alkylene chain having 1 to 6 C atoms;

X denotes one of the groups —O— or —S—;

$R^1$ denotes hydrogen or the radical —$COR_5$;

$R^2$ denotes an alkyl group having 1 to 6 C atoms, an alkenyl or alkynyl group in each case having 3 to 6 C atoms, an optionally substituted aralkyl group having 1 to 4 C atoms in the alkyl group and 6 to 10 C atoms in the aryl group or an optionally substituted aryl group having 6 to 10 C atoms;

$R^3$ and $R^4$ which may be identical or different, denote alkyl groups having 1 to 6 C atoms, alkenyl, alkynyl or cycloalkyl groups in each case having 3 to 6 C atoms, optionally substituted aralkyl groups having 1 to 4 C atoms in the alkyl group and 6 to 10 C atoms in the aryl group, optionally substituted aryl groups having 6 to 10 C atoms, heterocyclic groups having 3 to 5 ring C atoms and the group —S(O)$_m$— or $R^3$ and $R^4$, together with the nitrogen atom to which they are bonded, denote a heterocyclic ring of the formula

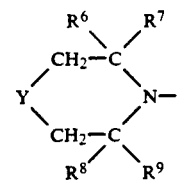

$R^5$ denotes an aliphatic radical having 1 to 6 C atoms, which may also be substituted by alkoxy having 1 to 6 C atoms or by an aliphatic thio radical having up to 4 C atoms; a cycloaliphatic radical having 5 to 7 C atoms; a bicycloaliphatic radical having 7 to 14 C atoms; a tricycloaliphatic radical having 7 to 16 C atoms; an alkoxy radical having 1 to 6 C atoms, which may also be substituted by alkoxy having 1 to 6 C atoms; an aryloxy radical having 6 to 10 C atoms; an alkoxycarbonyl radical having a total of 2 to 7 C atoms; an aryl radical having 6 to 10 C atoms; an aryl radical having 6 to 10 C atoms which is mono-, di- or tri-substituted by 1 to 3 halogen atoms and/or 1 to 3 alkyl radicals having 1 to 4 C atoms and/or 1 to 3 alkoxy radicals having 1 to 3 C atoms and/or 1 or 2 nitro groups and/or 1 or 2 hydroxyl groups and/or 1 or 2 alkylcarbonyloxy radicals having 1 to 4 C atoms and/or 1 to 3 alkylthio radicals having 1 to 4 C atoms and/or a trifluoromethyl radical and/or an imidazolyl radical; imidazolyl; pyridyl; thienyl; styryl;

m denotes one of the numbers 0, 1 or 2;

Y denotes one of the groups —(CH$_2$)$_n$—, —O—, —S(O)$_n$— or —N(R$^{10}$)—;

$R^6$, $R^7$, $R^8$ and $R^9$, which may be identical or different, denote hydrogen or alkyl groups having 1 to 4 C atoms;

n denotes one of the numbers 0, 1 or 2;

$R^{10}$ denotes an alkyl radical having 1 to 4 C atoms, an optionally substituted aryl radical having 6 to 12 C atoms or a radical of the formula —COOR$^{11}$, —COH, —COR$^{11}$ or —S(O)$_2$R$^{11}$;

$R^{11}$ denotes an alkyl radical having 1 to 4 C atoms.

The invention further relates to a process for the preparation of the compounds I according to the invention and to their use.

Aliphatic radicals, thio radicals, alkyl radicals, alkoxy radicals, alkenyl radicals and alkynyl radicals may be straight-chain or branched. This also applies if they occur as substituents of other radicals, e.g. as substituents of aryl radicals, or in connection with other radicals, e.g. as aralkyl, as alkoxycarbonyl, as alkylcarbonyloxy or as alkoxyalkoxy.

Aryl radicals may be unsubstituted or mono-, di- or trisubstituted by 1 to 3 halogen atoms and/or 1 to 3 alkyl radicals having 1 to 4 C atoms and/or 1 to 3 alkoxy radicals having 1 to 4 C atoms and/or 1 to 2 nitro groups and/or 1 to 3 hydroxyl groups and/or 1 to 3 alkylthio radicals having 1 to 4 C atoms and/or a trifluoromethyl radical. This also applies if they occur as substituents of other radicals, e.g. as aralkyl.

Examples of A are the methylene group, the ethylene group, the trimethylene group, the tetramethylene group, the methylene group substituted by a methyl group, an ethyl group or a propyl group, the ethylene group substituted by one, two or three methyl groups or the ethylene group substituted by one or two ethyl groups. The methylene group and the 1-methyl-ethylene group are particularly preferred for A.

Examples of $R^2$ are the methyl, the ethyl, the propyl, the butyl, the hexyl, the isopropyl, the sec-butyl, the isobutyl, the 2-propenyl, the 2-butenyl, the 3-butenyl, the 3-methyl-2-butenyl, the 2,3-dimethyl-2-butenyl, the 4-methyl-3-pentenyl, the 2-propynyl, the 2-butynyl, the 2-pentynyl, the 4-methyl-2-pentynyl, the benzyl, the 2-phenethyl, the 3-phenylpropyl, the 3-phenylbutyl, the 1-napthylmethyl, the 2-naphthylmethyl, the chlorobenzyl, the methylbenzyl, the methoxybenzyl, the ethoxybenzyl, the dimethoxybenzyl, the methylthiobenzyl, the trifluoromethylbenzyl, the phenyl, the 1-naphthyl, the 2-naphthyl, the chlorophenyl, the dichlorophenyl, the fluorophenyl, the tolyl, the methoxyphenyl, the ethoxyphenyl or the trifluoromethylphenyl group. Preferred groups for $R^2$ are alkyl groups having 1 to 6 C atoms, alkenyl and alkynyl groups in each case having 3 to 5 C atoms, aralkyl groups having 1 to 3 C atoms in the alkyl group and an unsubstituted or mono- or disubstituted phenyl radical as the aryl group and aryl groups which represent an unsubstituted, mono- or disubstituted phenyl radical. Groups which are particularly preferred are: ethyl, phenyl, benzyl and allyl.

Examples of the secondary amino group, which is formed by $R^3$ and $R^4$ and the nitrogen atom to which these radicals are bonded, are the dimethylamino, the diethylamino, the di-n-butylamino, the diisobutylamino, the dihexylamino, the tert.-butylmethylamino, the di-2-propenylamino, the di-2-propynylamino, the methyl-2-propynylamino, the dicyclohexylamino, the cyclohexylmethylamino, the dibenzylamino, the diphenethylamino, the benzylmethylamino, the diphenylamino, the methylphenylamino, the benzylphenylamino and the (1,1-dioxo-tetrahydrothiophene-3-yl)methylamino group. Examples of the heterocyclic ring group, which $R^3$ and $R^4$, together with the nitrogen atom to which they are bonded, can form are: the pyrrolidino, the 2,5-dimethylpyrrolidino, the 2,2,5,5-tetramethylpyrrolidino, the piperidino, the 2-methylpiperidino, the 2,2-dimethylpiperidino, the 2,6-dimethylpiperidino, the 2,2,6,6-tetramethylpiperidino, the perhydroazepin-1-yl, the morpholino, the 3,3-dimethylmorpholino, the 3,3,5,5-tetramethylmorpholino, the tetrahydro-1,4-thiazin-4-yl, the 1,1-dioxotetrahydro-1,4-thiazin-4-yl-, the 4-methyl-1-piperazinyl, the 4-propyl-1-piperazinyl, the 4-phenyl-1-piperazinyl, the 4-(2-methoxyphenyl)-1-piperazinyl, the 4-(methoxycarbonyl)-1-piperazinyl, the 4-(ethoxycarbonyl)-1-piperazinyl, the 4-formyl-1-piperazinyl, the 4-acetyl-1-piperazinyl or the 4-methanesulphonyl-1-piperazinyl group. $R^3$ and $R^4$ form, preferably together with the nitrogen atom to which they are bonded, a heterocyclic ring of the formula

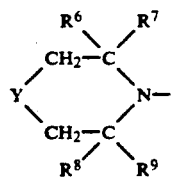

where Y denotes one of the groups $-(CH_2)_0-$ (i.e. a direct bond), $-(CH_2)_1-$, $-O-$, $-S-$, $-S(O)_2-$ and $R^6$, $R^7$, $R^8$ and $R^9$, which may be identical or different, denote hydrogen or alkyl radicals having 1 to 4 C atoms, particularly preferably hydrogen or methyl groups. Examples of particularly preferred heterocyclic rings are the pyrrolidino, the 2,5-dimethylpyrrolidino, the piperidino, the 2,2-dimethylpiperidino, the 2,6-dimethylpiperidino, the 2,2,6,6-tetramethylpiperidino, the morpholino, the 3,3-dimethylmorpholino, the 3,3,5,5-tetramethylmorpholino, the tetrahydro-1,4-thiazin-4-yl and the 1,1-dioxotetrahydro-1,4-thiazin-4-yl radical. The 2,6-dimethylpiperidino and the morpholino radical are very particularly preferred.

Suitable aliphatic radicals representing $R^5$ are in particular alkyl radicals, preferably having 1 to 4 C atoms. The aliphatic radicals representing $R^5$, in particular alkyl radicals, may also be substituted by alkoxy having 1 to 6 C atoms, in particular 1 to 4 C atoms, preferably 1 to 3 C atoms. Examples of alkyl and alkoxyalkyl radicals which may represent by $R^5$ are: methyl; ethyl; n-propyl; i-propyl; n-, i-, sec.- and tert.-butyl; n- and i-pentyl; n- and i-hexyl; methoxy, ethoxy, n-propoxy, i-propoxy, n-butoxy, i-butoxymethyl; 2-methoxy, 2-ethoxy, 2-n-propoxy, 2-i-propoxy, 2-n-butoxy-ethyl; 2-methoxy, 3-ethoxy, 3-n-propoxy, 3-i-propoxy-n-propyl or -i-propyl. The aliphatic radicals representing $R^5$, in particular the alkyl radicals, can also be substituted by an aliphatically substituted thio radical having up to 4 C atoms. Aliphatic thio radicals of this type are, for example, alkylthio radicals having 1 to 4 C atoms, such as, for example, methyl, ethyl, n-propyl, i-propyl, n-butyl, tert.-butyl-thio, but preferably allylthio ($CH_2=CH-CH_2-S-$). Suitable cycloaliphatic radicals representing $R^5$ are above all cycloalkyl radicals having 5 to 7 C atoms, in particular cyclopentyl, and preferably cyclohexyl. A suitable bicycloaliphatic radical representing $R^5$ is in particular 2,6,6-trimethylbicyclo(3.1.1)heptan-3-yl (=3-pinanyl). A suitable tricycloaliphatic radical representing $R^5$ is in particular tricyclo(3.3.1.1$^{3,7}$)decan-1-yl (=adamant-1-yl).

The alkoxy substituents of the alkoxy radicals have, in particular, 1 to 4 C atoms. Examples of alkoxy radicals and alkoxyalkoxy radicals which may represent $R^5$ are: methoxy; ethoxy; n- and i-propoxy; n-, i-, sec.- and tert.-butoxy; n-pentyloxy; i-hexyloxy; n-octyloxy; n-dodecyloxy; n-hexadecyloxy; n-heptadecyloxy; n-octadecyloxy; methoxy, ethoxy, n-propoxy, i-propoxy, n-butoxy-methoxy; 2-methoxy, 2-ethoxy, 2-n-propoxy, 2-i-propoxy-ethoxy; 3-methoxy, 3-ethoxy, 3-n-propoxy, 3-i-propoxy-propoxy; 4-methoxy, 4-ethoxy, 4-n-propoxy, 3-propoxy, or 4-n-butoxy-butoxy.

The alkoxycarbonyl radical representing $R^5$ preferably has 2 to 5 C atoms. Examples of this which may be mentioned are: methoxy, ethoxy, n-propoxy, i-propoxy, n-butoxy or i-butoxy-carbonyl. A suitable alkoxycarbonyl radical representing $R^5$ is in particular the ethoxycarbonyl radical.

Substituted and unsubstituted aryl radicals representing $R^5$ which may be mentioned are e.g. α- or β-naphthyl radicals, but in particular the phenyl radical. Aryloxy radicals representing $R^5$ which may be mentioned are e.g. α- or β-naphthoxy radicals, but in particular the phenoxy radical. The aryl radicals representing $R^5$ may be mono-, di- or trisubstituted, where, however, even on trisubstitution only a maximum of 2 nitro groups can be present, such as, for example, 2-methyl-4,6-dinitrophenyl and 2-chloro-6-methyl-4-nitrophenyl. With bulky substituents, only di- or mono-substitution may be possible. Suitable halogen substituents for the aryl radical are e.g. fluorine, chlorine and/or bromine atoms.

Alkylcarbonyloxy substituents for the aryl radicals, in particular for a phenyl radical, which may be mentioned e.g. are: acetoxy, n-propionyloxy, i-propionyloxy, n-butyryloxy or i-butyryloxy.

Examples of the optionally substituted aryl radicals representing $R^5$ are: phenyl, 2-, 3- or 4-methyl, -ethyl, -n-propyl, -i-propyl-phenyl; 2-, 3- or 4-methoxy, -ethoxy, -n-propoxy, -i-propoxyphenyl; 2-, 3- or 4-fluoro, -chloro or -bromo-phenyl; 2-, 3- or 4-nitrophenyl; 2-, 3- or 4-hydroxyphenyl; 2-, 3- or 4-acetoxy, -n-propionyloxy, -n-butyryloxyphenyl; 2,3-, 2,4-,2,5- or 2,6-dimethyl, -diethyl, -dipropyl-phenyl; 2- or 3-methyl-4-chlorophenyl; 2- or 3-ethyl-4-fluorophenyl; 2-chloro-4-ethylphenyl; 2-bromo-4-i-propylphenyl; 2,6-diethoxy-4-chlorophenyl; 2,3,4-, 3,4,5- or 2,3,5-trimethyl, -triethyl, -tripropyl, -trimethoxy, -triethoxy or tripropoxy-phenyl; 2-hydroxy-3-, -4- or -5-chlorophenyl; 2-methyl-3-, -4- or -5-acetoxy-phenyl.

Substituted aryl radicals representing $R^5$ which may be mentioned in particular are: methylphenyl (=tolyl), methoxyphenyl and chlorophenyl. The imidazolyl radical representing $R^5$ is preferably a 1-imidazolyl radical.

$R^5$ radicals which are preferred are: methyl, ethyl, cyclohexyl, phenyl, 4-chlorophenyl, 4-methoxyphenyl, methoxy, ethoxy, n-propoxy, i-propoxy, n-decyloxy, n-octadecyloxy, 2-n-propoxyethoxy, 2-i-propoxyethoxy, n-butoxymethyl, 2-n-butoxy-ethoxy and allylthiomethyl. Very particularly preferred for $R^5$ are ethoxy, phenyl and methoxyphenyl, in particular 4-methoxyphenyl.

The optionally substituted aryl radicals having 6 - 12 C atoms representing $R^{10}$ may be, for example, phenyl, 1-naphthyl, 2-naphthyl or biphenylyl radicals.

Preferred compounds of the formula I are those which contain one or, in particular, several of the preferred, above all the particularly preferred, radicals. Very particularly preferred compounds according to the invention are 4-benzylthiomethyl-3-(2,6-dimethylpiperidino)sydnone imine and 3-(2,6-dimethylpiperidino)-4-phenoxymethylsydnone imine and their pharmacologically acceptable acid addition salts, in particular their hydrochlorides.

A compound of the general formula I can be prepared by a process in which a substituted N-nitrosoaminoacetonitrile compound of the general formula II

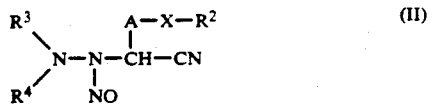

in which A, X, $R^2$, $R^3$ and $R^4$ have the meanings already mentioned, is cyclized to a compound of the general formula Ia

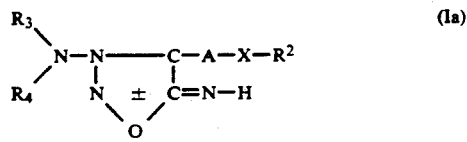

and in which this or an acid addition salt thereof in the case in which a compound of the formula I with $R^1 = -COR^5$ is intended to be prepared, is acylated with an acylating agent which introduces the radical $-COR^5$, and the compound thus obtained is optionally converted into a pharmacologically acceptable acid addition salt.

The cyclization of the compound II to the compound Ia is carried out in a suitable organic or inorganic solvent, dispersant or diluent with the addition of a cyclizing agent, normally at temperatures from $-10°$ to $40°$ C., in particular $0°$ to $40°$ C., preferably at $0°$ to $20°$ C.

Suitable cyclizing agents are those which give a pH of 3 or below in aqueous solution, that is e.g. strong acids, such as mineral acids, such as sulphuric, nitric or phosphoric acid, preferably hydrogen chloride, but also strong organic acids, such as sulphonic acids or trifluoroacetic acid. The cyclization is normally carried out with ice-cooling. 0.1 to 10 moles, preferably 1 to 5 moles, of the cyclizing agent are used e.g. relative to 1 mole of the compound of the formula II. The cyclizing agent is normally employed in excess. The use of hydrogen chloride as the cyclizing agent, which is normally led into the reaction mixture until it is saturated, is particularly convenient. The corresponding acid addition salt of the compound Ia is normally obtained in the cyclization.

Suitable solvents, dispersants or diluents are e.g.: alcohols, for example those having 1 to 8 C atoms, in particular those having 1 to 6 C atoms, preferably those having 1 to 4 C atoms, such as e.g. methanol, ethanol, i- and n-propanol, i-, sec- and tert-butanol, n-, i-, sec-, tert-pentanol, n-hexanol, 2-ethylbutanol, 2-ethylhexanol, isooctyl alcohol, cyclopentanol, cyclohexanol, methylcyclohexanol (mixture), benzyl alcohol; ethers, in particular those having 2 to 8 C atoms in the molecule, such as e.g. diethyl ether, methyl ethyl ether, di-n-propyl ether, di-isopropyl ether, methyl-n-butyl ether, methyl tert-butyl ether, ethyl propyl ether, di-butyl ether, tetrahydrofuran, 1,4-dioxane, 1,2-dimethoxyethane, bis-$\beta$-methoxyethyl ether; oligoethylene glycol dimethyl ethers, such as e.g. tetraglyme or pentaglyme; carboxylic acid alkyl esters, in particular those having 2 to 10 C atoms in the molecule, such as e.g. methyl, ethyl, butyl or isobutyl formates, methyl, ethyl, propyl, isopropyl, butyl, isobutyl or sec-butyl, amyl, isoamyl, hexyl, cyclohexyl or benzyl acetates, methyl, ethyl or butyl propionates; ketones, in particular those having 3 to 10 C atoms in the molecule, such as e.g. acetone, methyl ethyl ketone, methyl n-propyl ketone, diethyl ketone, 2-hexanone, 3-hexanone, di-n-propyl ketone, di-iso-propyl ketone, di-iso-butyl ketone, cyclopentanone, cyclohexanone, methylcyclohexanone, dimethylcyclohexanone, benzophenone, acetophenone; aliphatic hydrocarbons, such as e.g. hexane, heptane, low- and high-boiling petroleum ethers, petroleum spirits and white spirit; cycloaliphatic hydrocarbons, such as e.g. cyclopentane, cyclohexane, methylcyclohexane, tetralin, decalin; aromatic hydrocarbons, such as e.g. benzene, toluene, o-, m- and p-xylene, ethylbenzene; halogenated aliphatic or aromatic hydrocarbons, such as e.g. methylene chloride, chloroform, carbon tetrachloride, 1,2-dichloroethane, chlorobenzene, dichlorobenzene; hexamethylphosphoramide; sulphoxides, such as e.g. dimethyl sulphoxide; tetramethylene sulphone; water. Mixtures of various solvents or dispersants can also be used, for example water/methanol or preferably ethyl acetate/methanol.

The compounds of the formula Ia represent compounds of the general formula I according to the invention in the case in which $R^1$ is hydrogen.

The acylation of the compound of the formula Ia, which may also be present in the form of an acid addition salt, to introduce the radical $R^1 = -COR^5$ can be carried out in a manner known per se using a suitable acylating agent of the formula III

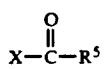
(III)

in which X represents a radical which can be eliminated by a nucleophile.

In the formula III, X denotes e.g., in particular, halogen, preferably —Cl or —Br; —OH; —O—alkyl, in particular having 1 to 5 C atoms; —O—aryl, where the aryl radical is in particular a phenyl radical, which may also be mono- or polysubstituted by alkyl, in particular methyl, and/or nitro, and, for example, is a tolyl, dinitrophenyl or nitrophenyl radical; —O—CO—$R^5$; —O—CO—O—alkyl, in particular having 1 to 5 C atoms in the alkyl radical, or the radical of an azole or benzazole having at least 2 N atoms in the quasi-aromatic 5-membered ring, which is bonded via an N atom.

The acylation is expediently carried out in the liquid phase in the presence of an inert solvent, dispersant or diluent or in an excess of the acylating agent, expediently with stirring.

The acylating agent of the formula III is expediently employed in the acylation in an equivalent amount or in a small molar excess. Excesses of up to 30 mol% are as a rule sufficient, i.e. the molar ratio between the compound of the formula Ia and the acylating agent of the formula III is expediently 1:(1 to 1.3), preferably 1:(1 to 1.2). If an acid is eliminated in the acylation reaction, the addition of an acid scavenger, such as e.g. an alkali metal hydroxide, such as e.g. sodium hydroxide, potassium hydroxide or lithium hydroxide, a tertiary organic amine, such as e.g. pyridine or triethylamine, an alkali metal carbonate or alkali metal bicarbonate, such as e.g. sodium carbonate or sodium bicarbonate, or an alkali metal salt of a weak organic acid, such as e.g. sodium acetate, is expedient. Suitable catalysts, such as e.g. 4-dimethylaminopyridine, may also be added during the acylation reaction.

The acylation can in principle be carried out at temperatures between −10° C. and the boiling point of the solvent, dispersant or diluent used. In many cases, the reaction is carried out at 0° to 50° C., in particular at 0° to 30° C. and preferably at room temperature.

The compounds of the formula III are acylating agents and thus represent e.g.: for X = halogen: acid halides or haloformic acid esters, of which acid chlorides and chloroformic acid esters are preferred; for —OH: carboxylic acids; for —O—alkyl and —O—aryl: esters, of which the tolyl, 2,4-dinitro or 4-nitrophenyl esters are preferred; for —O—CO—$R^5$: anhydrides; for —O—CO—O—alkyl: mixed carboxylic acid/carbonic acid anhydrides; or heterocyclic amides or azolides. The acylating agents of the formula III can be prepared by processes known per se.

When using a carboxylic acid as the acylating agent, the addition of an activating agent, which has the object of increasing or activating the acylating potential of the carboxylic acid, or of converting the carboxylic acid into a reactive carboxylic acid derivative of the formula III in situ or preferably shortly before the reaction with the compound of the formula Ia is expedient. Suitable activating agents of this type are e.g.: N,N'-disubstituted carbodiimides, in particular if they contain at least one secondary or tertiary alkyl radical, such as e.g. diisopropyl-, dicyclohexyl- or N-methyl-N'-tert.butyl-carbodiimide (compare Methodicum Chimicum, Verlag G. Thieme, Stuttgart, Vol. 6, (1974), p. 682/683, and Houben-Weyl, Methoden der Org. Chemie (Methods of organic chemistry), Vol. 8, (1952), p. 521/522); carbonic acid derivatives, such as e.g. phosgene, chloroformic acid esters, in particular having 1 to 5 C atoms in the alkyl radical (compare e.g. Tetrahedron Letters 24 (1983), 3365 to 3368); carbonic acid esters, such as e.g. N,N'-disuccinimidyl carbonate, diphthalimidyl carbonate, 1,1'-(carbonyldioxy)-dibenzo-triazole or di-2-pyridyl carbonate (compare e.g. Tetrahedron Letters, Vol. 25, No. 43, 4943-4946), if appropriate in the presence of suitable catalysts, such as e.g. 4-dimethylaminopyridine. N,N'-carbonyldiazoles, such as e.g. N,N'-carbonyl-diimidazole, 2,2'-carbonyl-1,2,4-ditriazole, 1,1'-carbonyl-1,2,3-ditriazole, N,N'-carbonyl-dipyrazole, 2,2'-carbonyl-ditetrazole, N,N'-carbonyl-benzimidazole or N,N'-carbonylbenzotriazole are further suitable as activating agents (compare e.g. H. A. Staab, M. Lücking and F. H. Dürr, Chem. Ber. 95, (1962), 1275 et seq., H. A. Staab and A. Mannschreck, Chem. Ber. 95, (1962), 1284 et seq. H. A. Staab and W. Rohr, "Syntheses with heterocyclic amides (zolides)" in "Neuere Methoden der Präparativen Organischen Chemie" (Newer Methods of Preparative Organic Chemistry), Volume V, Verlag Chemie, 1967, p. 53 et seq., in particular p. 65 to 69). The commercially available N,N'-carbonyldiimidazole is frequently used as the N,N'-carbonyldiazole. However, the other N,N'-carbonylazoles are also easily accessible from the respective azole and phosgene.

Further suitable activating agents for carboxylic acids are: derivatives of oxalic acid, such as e.g. oxalyl chloride (compare e.g. GB-PS 2,139,225) or N,N'-oxalyl-diazoles such as e.g. 1,1'-oxalyldi-imidazole, 1,1'-oxalyldi-1,2,4-triazole and 1,1'-oxalyldi-1,2,3,4-tetrazole (compare e.g. Shizuaka Murata, Bull. Chem. Soc. Jap. 57, 3597-3598 (1984)); methylethylphosphinic anhydride (compare e.g. DE-OS 3,101,427); diphosphorus tetraiodide (Chem. Lett. 1983, 449); dialkyl disulphite (Indian J. Chem. 21, 259 (1982)); or other reactive agents.

Suitable solvents, dispersants or diluents for the acylation are e.g. those which have been given for carrying out the cyclization, moreover also e.g. pyridine and amides, such as e.g. dimethylformamide. In addition to water, polar organic solvents, such as dimethylformamide, dimethyl sulphoxide or pyridine are preferred for the acylation. Solvent mixtures, such as e.g. a mixture of water and methylene chloride, are also suitable.

The compounds of the formula I according to the invention can optionally exist in the form of different stereoisomers. The invention includes both the possible individual steroisomers of the formula I and mixtures of several stereoisomers of the formula I with any composition. The preparation of specific isomers can be carried out by processes known per se. For example, individual optically active isomers of compounds of the formula I can be obtained by chiral synthesis or separation of racemic mixtures.

The substituted 3-amino-sydnone imines of the general formula I can form acid addition salts with inorganic or organic acids. Pharmacologically acceptable acid addition salts are preferred. Inorganic or organic acids are suitable for the formation of acid addition salts of this type. Suitable acids are, for example, hydrogen chloride, hydrogen bromide, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acid or naphthalenedisulphonic acids, in particular 1,5-naphthalenedisulphonic acid. The acid addition salts may be prepared as is customary, by combining the components, expediently in a suitable solvent or diluent. The acid addition salts are obtained in the synthesis of the compounds of the formula Ia. The free compounds of the formula I can optionally be isolated from the acid addition salts in a manner known per se, e.g. by dissolving in water and carefully adding an alkali.

The substituted N-nitrosoamino-acetonitriles of the formula II required as starting materials can be prepared by a process in which a) a compound of the general formula IV

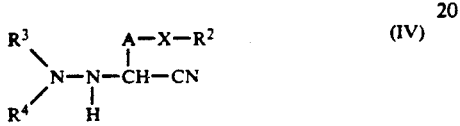

in which A, X, $R^2$, $R^3$ and $R^4$ have the meanings already mentioned, is nitrosated, or in which b) an acid addition salt of a compound of the formula Ia is reacted with a base.

The compounds of the formula IV can be prepared in a manner known per se by the Strecker's aminonitrile synthesis from compounds of the general formula V

in which $R^3$ and $R^4$ have the meanings already mentioned, by reaction with an aldehyde of the general formula VI

or the masked form of such an aldehyde, e.g. an acetal of the formula VII

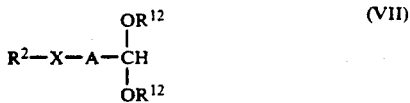

in which $R^{12}$ represents a straight-chain or branched alkyl radical having 1 to 4 C atoms or a benzyl radical or the two radicals $R^{12}$ together represent a di- or trimethylene bridge optionally substituted by alkyl groups, and hydrocyanic acid or a suitable cyanide, e.g. sodium cyanide or a silyl cyanide, in a suitable solvent, e.g. water.

The nitrosation of the compound of the formula IV is carried out in a known manner, expediently in a suitable inert solvent or solvent mixture, preferably in water, normally at temperatures from 0° to 40° C. and preferably at temperatures from 0° to 10° C. The nitrosation is carried out e.g. with nitrous acid, NO, NOCl or NO-containing gas mixtures. The nitrosation is expediently carried out with nitrous acid, which is advantageously generated from an alkali metal nitrite, e.g. sodium nitrite, and an acid, in particular hydrochloric acid. It is expedient to adjust the aqueous solution of the compound IV to a pH of 1 to 3 with an acid, in particular hydrochloric acid, and to add the alkali metal nitrite dropwise in the form of an aqueous solution to the stirred and cooled solution of the compound.

The compound II can be isolated from the solution of the compound II thus formed, or the solution of the compound II can be subjected to the cyclization reaction directly. Normally, however, it is appropriate, for the subsequent cyclization, to take up the nitroso compound II first in a suitable organic solvent and to carry out the cyclization to the compound of the formula Ia in it, optionally after addition of a further solvent.

The compounds of the general formula V are known in some cases or can be prepared, starting from compounds of the general formula VIII

by a process in which either a) a compound of the formula VIII is nitrosated to give the N-nitroso compound VIIIa and this is then reduced with a suitable reducing agent, for example lithium aluminium hydride:

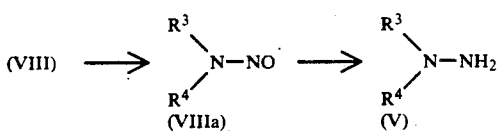

or which in a manner known per se b) a compound of the formula VIII is converted with potassium cyanate in acid medium into the urea derivative and this is then converted by oxidation with sodium hypochlorite by means of the Hoffmann degradation into the compound V:

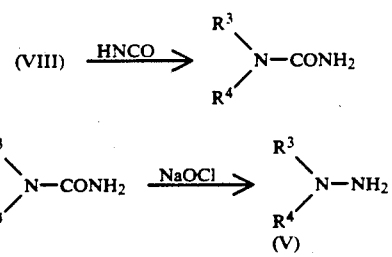

Compounds of the general formula VI are known in some cases or can be prepared in a manner known per se by a process in which, for example, either a) an acetal of the formula VII is cleaved in acidic medium

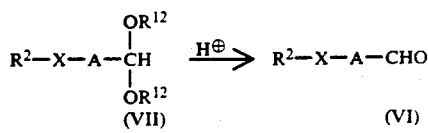

or in which b) a nucleophile of the formula IX, in which $R^2$ and X have the meaning already mentioned, is added to the double bond of an aldehyde of the formula X, where A' represents an alkenyl radical and by formal addition of a hydrogen atom changes into the alkylene chain A with its already mentioned meaning:

Compounds of the general formula VII are known in some cases or can be prepared in a manner known per se by a process in which, for example, either a) an acetal of the formula XI, in which Z represents a nucleofugic group, for example a chlorine or a bromine atom, is reacted with a nucleophile of the formula IX

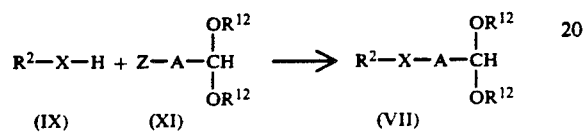

or in which b) an acetal of the formula XIII is alkylated with an electrophile of the formula XII, in which Z has the meaning already mentioned:

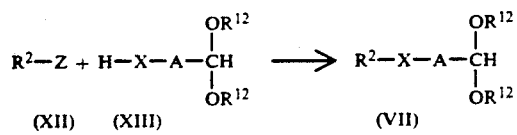

Compounds of the formula II can also be prepared by a process in which an acid addition salt of a compound of the formula Ia, expediently in aqueous solution, is treated with a base, i.e. a compound which gives an alkaline reaction in water, such as e.g. an alkali metal hydroxide, such as e.g. lithium hydroxide, sodium hydroxide or potassium hydroxide, an alkali metal carbonate, such as e.g. lithium carbonate, potassium carbonate or sodium carbonate or an alkali metal bicarbonate, such as e.g. sodium bicarbonate, or an amine, in particular a tertiary amine, such as e.g. triethylamine. The reaction is normally carried out at 10° to 40° C., preferably at room temperature. At least so much base is added that the acid radical is completely bound As a rule, the acid addition salt is dissolved in water or a mixture of water and solvent, and a quantity of base is added such that the aqueous solution gives an alkaline reaction. The binding of the acid radical can also be carried out using an exchanger resin.

The compounds of the formula II can also form acid addition salts with inorganic or organic acids, of which pharmacologically acceptable acid addition salts are preferred In relation to the formation of these acid addition salts and suitable acids, the points already stated for the acid addition salts of the compound I apply.

The compounds of the general formulae I and II and their pharmacologically acceptable acid addition salts have useful pharmacological properties. Their effect on the cardiovascular system is particularly pronounced.

Compared with known 3-aminosydnone imines unsubstituted in the 4-position, e.g. the commercial product molsidomine, or 3-aminosydnone imines substituted in the 4-position by an alkyl or aralkyl group, the compounds of the general formula I containing an ether or thioether group in the 4-substituent have a longer duration of action and/or higher potency. The same applies to the compounds of the formula II in comparison with other N-nitrosoaminoacetonitriles. The compounds of the formulae I and II and their pharmacologically acceptable acid addition salts lower, for example, the blood pressure as well as the pulmonary artery pressure and the left ventricular end-diastolic pressure, and thus contribute to relieving the load on the heart in the sense of an antianginal action, without provoking reflex tachycardia at the same time.

The compounds of the formulae I and II and their pharmacologically acceptable acid addition salts may therefore be administered to humans as medicaments alone, in mixtures with one another or in the form of pharmaceutical preparations which allow enteral or parenteral use and which contain an effective dose of at least one compound of the formulae I and II or an acid addition salt thereof as active constituent, in addition to customary pharmaceutically acceptable excipients and additives.

The medicaments may be administered orally, e.g. in the form of pills, tablets, lacquered tablets, coated tablets, hard and soft gelatin capsules, solutions, syrups, emulsions or suspensions or aerosol mixtures However, administration may also take place rectally, e.g. in the form of suppositories, or parenterally, e.g. in the form of injection solutions, or percutaneously, e.g. in the form of ointments or tinctures In order to prepare the pharmaceutical preparations, pharmaceutically inert inorganic or organic excipients may be used. For the preparation of pills, tablets, coated tablets and hard gelatin capsules, e.g. lactose, maize starch or derivatives thereof, talc, stearic acid or salts thereof etc. may be used. Excipients for soft gelatin capsules and suppositories are e.g. fats, waxes, semisolid and liquid polyols, natural or hardened oils etc. Suitable excipients for the preparation of solutions and syrups are e.g. water, sucrose, dextrose, glucose, polyols etc. Suitable excipients for the preparation of injection solutions are e.g. water, alcohols, glycerol, polyols or vegetable oils.

In addition to the active compounds and excipients, the pharmaceutical preparations may further contain additives such as e.g. fillers, extenders, disintegrants, binders, lubricants, wetting agents, stabilizers, emulsifiers, preservatives, sweeteners, colorants, flavourings or aromatizers, buffer substances, and in addition solvents or solubilizers or agents for achieving a depot effect, and also salts for changing the osmotic pressure, coating agents or antioxidants. They may also contain two or more compounds of the formulae I and/or II or their pharmacologically acceptable acid addition salts and other therapeutically active substances.

Other therapeutically active substances of this type are, for example: β-receptor blockers such as e.g. propranolol, pindolol, metoprolol; vasodilators such as e.g. carbochromen; sedatives such as for example barbituric acid derivatives, 1,4-benzodiazepines and meprobamate; diuretics such as e.g. chlorothiazide; cardiotonic agents such as e.g. digitalis preparations; hypotensive agents such as e.g. hydralazine, dihydralazine, prazosine, clonidine, Rauwolfia alkaloids; agents which lower the fatty acid level in the blood such as e.g. bezafibrate, fenofibrate; and agents for thrombosis prophylaxis such as e.g. phenprocoumon.

The content of the active compound or the active compounds of the formula I in the pharmaceutical preparations can vary within wide limits and is e.g. 0.05 to 50% by weight, preferably 0.05 to 20% by weight. In solid administration forms, such as coated tablets, tablets etc., the content of one or more active compounds of the formula I is in many cases 2 to 20% by weight. Liquid administration forms, such as drops, emulsions and injection solutions frequently contain 0.05 to 2% by weight, preferably 0.05 to 1% by weight of one or more active compounds of the formula I. The content of one or more active compounds of the formula I may partly be replaced in the pharmaceutical preparations, e.g. up to 50% by weight, preferably up to 5 to 40% by weight, by one or more other therapeutically active substances.

The compounds of the formulae I and/or II, their pharmacologically acceptable acid addition salts and pharmaceutical preparations which contain the compounds of the formula I and/or II or their pharmacologically acceptable acid addition salts as active compounds, may be used in humans in the control or prophylaxis of disorders of the cardiovascular system, for example as antihypertensive medicaments in the various forms of high blood pressure, and in the control or prophylaxis of angina pectoris etc. The dosage may vary within wide limits and is to be adjusted to the individual conditions in each individual case. In general, a daily dose of about 0 5 to 500 mg, preferably 1 to 100 mg, per human individual is suitable for oral administration. With other administration forms the daily dose, on account of the good absorption of the active compounds, also lies in similar dose ranges, i.e in general also at 0.5 to 100 mg/human. The daily dose is normally divided into a number of, for example 2 to 4, part administrations.

The pharmacological action of the compounds of the formula I was determined by a modified method of Godfraind and Kaba (Arch. Int. Pharmacodyn. Ther. 196, (Suppl ) 35 to 49, 1972) and of Schüman et al. (Naunyn-Schmiedeberg's Arch. Pharmacol. 289, 409 to 418, 1975). In this connection, spiral strips of the pulmonary artery of the guinea pig are depolarized using 40 mmol/l of potassium after equilibration in calcium-free Tyrode solution. An addition of 0.5 mmol/1 of $CaCl_2$ then induces a contraction. The relaxant effect of the test substance is determined by cumulative addition in semilogarithmic graduated concentrations. The concentration of the test substance which inhibits the contraction by 50% (=$IC_{50}$, mol/l) is determined from the concentration-effect curve (abscissa: —log mol/l of test substance, ordinate % inhibition of the maximum contraction, average value of 4 to 6 vessel strips). The $IC_{50}$ values thus obtained are indicated in the following table. As the comparison with the $IC_{50}$ value of $>3.10^{-4}$ for the known compound molsidomine (N-ethoxycarbonyl-3-morpholino-sydnone imine), compare DE-B-1,695,897, shows, the values for the compounds of the formula I are considerably more favourable.

TABLE

| Compound (Example No.) | $IC_{50}$ (mol/l) | |
| --- | --- | --- |
| 5 | 1.1 | $10^{-6}$ |
| 7 | 0.7 | $10^{-6}$ |
| 8 | 0.8 | $10^{-6}$ |
| 10 | 2.0 | $10^{-6}$ |
| 12 | 0.5 | $10^{-6}$ |

TABLE-continued

| Compound (Example No.) | $IC_{50}$ (mol/l) | |
| --- | --- | --- |
| 13 | 2.0 | $10^{-6}$ |
| molsidomine | >3.0 | $10^{-4}$ |

EXAMPLE 1

3-(2.6-Dimethylpiperidino)-4-ethylthiomethyl-sydnone imine hydrochloride a)

2-(2,6-Dimethylpiperidino)amino-3-ethylthiopropionitrile

A solution of 4.9 g of sodium cyanide in 20 ml of water is added dropwise at 0° to 5° C. to a solution of 16.5 g of 1-amino-2,6-dimethylpiperidine hydrochloride in 50 ml of water, then 11.4 g of ethylthioacetaldehyde are added dropwise in the course of 30 min. The pH of the reaction mixture is adjusted to 7 with hydrochloric acid. After stirring overnight, the mixture is extracted with dichloromethane, and the combined extracts are dried and concentrated in a rotary evaporator. 21.6 g of 2-(2,6-dimethylpiperidino)amino-3-ethylthiopropionitrile are obtained, which are employed in the following step without further purification.

b)

3-(2,6-Dimethylpiperidino)-4-ethylthiomethyl-sydnone imine hydrochloride

A solution of 3.9 g of sodium nitrite in 20 ml of water is added dropwise with ice-cooling to a mixture of 21.6 g of the ethylthiopropionitrile described under a), 50 ml of water and 5.1 ml of concentrated hydrochloric acid. After stirring at 0°-5° C. for 2 hours, the mixture is extracted with ethyl acetate, and the combined extracts are dried and partly concentrated. After addition of 100 ml of methanolic hydrogen chloride solution, hydrogen chloride is passed in with ice-cooling for 2 hours. The solution is concentrated in a rotary evaporator, the residue is stirred with acetone, the precipitate is filtered off with suction, the filtrate is concentrated in a rotary evaporator, the residue is stirred several times with ethyl acetate and the precipitate is filtered off with suction. The combined precipitates are recrystallized from acetonitrile. 7.7 g of 3-(2,6-dimethylpiperidino)-4-ethylthiomethylsydnone imine hydrochloride of melting point 132° C. (dec.) are obtained.

EXAMPLE 2

3-(2,6-Dimethylpiperidino)-N-ethoxycarbonyl-4-ethylthiomethylsydnone imine 1.5 g of sodium hydrogen carbonate are added with ice-cooling to 2.5 g of the 3-(2,6-dimethylpiperidino)-4-ethylthiomethylsydnone imine hydrochloride described under 1) in 25 ml of water and 10 ml of dichloromethane, then a solution of 1.0 g of ethyl chloroformate in 5 ml of dichloromethane is added dropwise. After stirring for 2 hours, the organic phase is separated off, the aqueous phase is extracted with dichloromethane, and the combined organic phases are dried and concentrated in a rotary evaporator. The residue is recrystallized from hexane Yield: 2.3 g of 3-(2,6-dimethylpiperidino)-N-ethoxycarbonyl-4-ethylthiomethylsydnone imine of melting point 54° C.

EXAMPLE 3

N-Benzoyl-3-(2,6-dimethylpiperidino)-4-ethylthiomethylsydnone imine 2.5 g of the 3-(2,6-dimethylpiperidino)-4-ethylthiomethylsydnone imine hydrochloride described under 1) are acylated with 1.3 g of benzoyl chloride in dichloromethane/water in the presence of 1.4 g of sodium hydrogen carbonate analogously to 2). The product obtained is purified by chromatography on silica gel using dichloromethane/methanol (98:2). 0.7 g of N-benzoyl-3-(2,6-dimethylpiperidino)-4-ethylthiomethylsydnone imine is obtained as a colourless oil.

EXAMPLE 4

4-Allylthiomethyl 3-(2,6-dimethylpiperidino)sydnone imine hydrochloride a)
3Allylthio-2-((2,6-dimethylpiperidino)amino)propionitrile

A solution of 9.5 g of allylthioacetaldehyde diethyl acetal in 10 ml of methanol is added dropwise to a mixture of 6.0 g of 1-amino-2,6-dimethylpiperidine, 30 ml of water and 5.6 ml of concentrated hydrochloric acid. After stirring for 2 hours, a solution of 2.5 g of sodium cyanide in 20 ml of water is added dropwise at 0° C. The pH is adjusted to 7 with sodium hydrogen carbonate solution and the reaction mixture is stirred overnight. The mixture is extracted with dichloromethane, and the combined extracts are dried and concentrated in a rotary evaporator. 12.3 g of 3-allylthio-2-((2,6-dimethylpiperidino)amino)-propionitrile are obtained, which are employed in the following step without further purification.

b)
4-Allylthiomethyl-3-(2,6-dimethylpiperidino)sydnone imine hydrochloride A solution of 3.3 g of sodium nitrite in 20 ml of water is added dropwise at 0°-5° C. to a mixture of 12.0 g of the aminonitrile intermediate described under a), 50 ml of water and 4.1 ml of concentrated hydrochloric acid. After stirring at 0° C. for 3 hours, the mixture is extracted with ethyl acetate, the combined extracts are dried and partly concentrated, and 50 ml of methanolic hydrogen chloride solution are added. Hydrogen chloride is passed in for 1.5 h, the solution is concentrated in a rotary evaporator, the residue is stirred with acetonitrile, the precipitate is filtered off with suction, the filtrate is concentrated in a rotary evaporator and the residue is chromatographed on silica gel using dichloromethane/methanol (9:1). After triturating with acetone/diethyl ether and filtering off with suction, 2.2 g of 4-allylthiomethyl-3-(2,6dimethylpiperidino)-sydnone imine hydrochloride are obtained, which melt at 151°-152° C. (dec.).

EXAMPLE 5

3-(2,6-Dimethylpiperidino)-4-phenylthiomethylsydnone imine hydrochloride a)
2-(2,6-Dimethylpiperidino)amino-3-phenylthiopropionitrile 8.6 g of 1-amino-2,6-dimethylpiperidine hydrochloride, 2.6 g of sodium cyanide and 7.9 g of phenylthioacetaldehyde are reacted analogously to 1a). 13.0 g of 2-(2,6-dimethylpiperidino)-amino-3-phenylthiopropionitrile are obtained, which are employed in the following step without further purification.

b)
3-(2,6-Dimethylpiperidino)-4-phenylthiomethylsydnone imine hydrochloride 13.0 g of the propionitrile intermediate described under a) are reacted with 3.1 g of sodium nitrite in the presence of 3.9 ml of concentrated hydrochloric acid analogously to 1b). The crude product obtained after cyclization with hydrogen chloride is chromatographed on silica gel using dichloromethane/methanol (9:1) and recrystallized from acetone/acetonitrile.

Yield: 4.3 g of 3-(2,6-dimethylpiperidino)-4-phenylthiomethylsydnone imine hydrochloride of melting point 164°-165° C. (dec.)

EXAMPLE 6

N-Benzoyl-3-(2,6-dimethylpiperidino)-4-phenylthiomethylsydnone imine 0.6 g of N-benzoyl-3-(2,6-dimethylpiperidino)-4-phenylthiomethylsydnone imine are obtained as an oil from 1.4 g of the 3-(2,6-dimethylpiperidino)-4-phenylthiomethylsydnone imine hydrochloride described under 5), 0.6 g of benzoyl chloride and 0.7 g of sodium hydrogen carbonate in dichloromethane/water analogously to 3).

EXAMPLE 7

4-Benzylthiomethyl-3-morpholinosydnone imine hydrochloride a) 3-Benzylthio-2-(morpholinoamino)propionitrile A solution of 4.9 g of sodium cyanide in 30 ml of water is added dropwise with ice-cooling to a mixture of 10.3 g of 4-aminomorpholine, 50 ml of water and 8.6 ml of concentrated hydrochloric acid. A solution of 16.6 g of benzylthioacetaldehyde in 20 ml of methanol is then added dropwise and the reaction mixture is stirred overnight. The methanol is stripped off on a rotary evaporator, the aqueous solution is extracted with dichloromethane, and the combined extracts are dried and concentrated in a rotary evaporator. 24.9 g of 3-benzylthio-2-(morpholinoamino)-propionitrile remain, which are employed in the following step without further purification.

b) 4-Benzylthiomethyl-3-morpholinosydnone imine hydrochloride

A solution of 6 2 g of sodium nitrite in 20 ml of water is added dropwise at 0°-5° C. to a mixture of 24.8 g of the benzylthiopropionitrile described under a), 50 ml of water and 7.7 ml of concentrated hydrochloric acid. After stirring for 1 hour, the pH is adjusted to 5 with sodium hydrogen carbonate solution, the solution is extracted with ethyl acetate, the combined extracts are dried and partly concentrated, and 100 ml of methanolic hydrogen chloride solution are added. Hydrogen chloride is passed in with ice-cooling for 5 h, the mixture is partly concentrated, the precipitate deposited is filtered off with suction, the filtrate is further concentrated, and the precipitate is filtered off with suction and stirred with acetone. The residue is recrystallized from isopropanol.

Yield: 6.9 g of 4-benzylthiomethyl-3-morpholinosydnone imine hydrochloride as the hemihydrate of melting point 165°-167° C. (dec.).

EXAMPLE 8

4-Benzylthiomethyl-3-(2,6-dimethylpiperidino)sydnone imine hydrochloride a)
3-Benzylthio-2-((2,6-dimethylpiperidino)amino)propionitrile

A solution of 2.8 g of sodium cyanide in 20 ml of water and a solution of 9.6 g of benzylthioacetaldehyde in 20 ml of methanol are added dropwise to a mixture of 7.4 g of 1-amino-2,6-dimethylpiperidine, 60 ml of water and 4.9 ml of concentrated hydrochloric acid. The pH is brought to 7 with hydrochloric acid, and the reaction mixture is stirred overnight and extracted with dichloromethane. The combined extracts are washed with water, containing acetic acid, of pH 4-5, dried and concentrated in a rotary evaporator. 14.9 g of 3-benzylthio-2-((2,6-dimethylpiperidino)amino)propionitrile are obtained which are reacted further without further purification.

b)
4-Benzylthiomethyl-3-(2,6-dimethylpiperidino)sydnone imine hydrochloride

A solution of 3.6 g of sodium nitrite in 25 ml of water is added dropwise with ice-cooling to a mixture of 14.8 g of the aminopropionitrile described under a), 50 ml of water and 4.3 ml of concentrated hydrochloric acid. After stirring at 0°-5° C. for 2 hours, the mixture is extracted with ethyl acetate, the combined extracts are dried and partly concentrated, and 50 ml of methanolic hydrogen chloride solution are added. Hydrogen chloride is passed in with ice-cooling for 1 h. The precipitate deposited is filtered off with suction, the filtrate is concentrated in a rotary evaporator and the residue is chromatographed on silica gel using dichloromethane/methanol (95:5). 6.2 g of 4-benzylthiomethyl-3-(2,6-dimethylpiperidino)-sydnone imine hydrochloride are obtained, which melt at 150 to 152° C. with decomposition after recrystallization from acetone.

EXAMPLE 9

4-Benzylthiomethyl-3-(2,6-dimethylpiperidino)-N-ethoxycarbonylsydnone imine 2.7 g of the 4-benzylthiomethyl-3-(2,6-dimethylpiperidino)sydnone imine hydrochloride described under 8) are reacted with 1.0 g of ethyl chloroformate in the presence of 1.2 g of sodium hydrogen carbonate analogously to 3). 2.4 g of 4-benzylthiomethyl-3-(2,6-dimethylpiperidino)-N-ethoxycarbonylsydnone imine are obtained as an oil.

EXAMPLE 10

N-Benzoyl-4-benzylthiomethyl-3-(2,6-dimethylpiperidino)sydnone imine 2.0 g of the 4-benzylthiomethyl-3-(2,6-dimethylpiperidino)sydnone imine hydrochloride described under 8) are reacted with 0.9 g of benzoyl chloride in the presence of 1.0 g of sodium hydrogen carbonate analogously to 2). 1.7 g of N-benzoyl-4-benzylthiomethyl-3-(2,6-dimethylpiperidino)sydnone imine of melting point 98 to 100° C. are obtained by recrystallization from hexane.

EXAMPLE 11

4-Benzylthiomethyl-3-(2,6-dimethylpiperidino)-N-(4-methoxybenzoyl)sydnone imine 2.1 g of the 4-benzylthiomethyl-3-(2,6-dimethylpiperidino)sydnone imine hydrochloride described under 8) are reacted with 1.4 g of 4-methoxybenzoyl chloride in the presence of 1.1 g of sodium hydrogen carbonate analogously to 3). 0.7 g of 4-benzylthiomethyl-3-(2,6-dimethylpiperidino)-N-(4-methoxybenzoyl)-sydnone imine of melting point 104° C. are obtained.

EXAMPLE 12

4-(2-Benzylthio-1-methylethyl)-3-morpholinosydnone imine hydrochloride a)
4-Benzylthio-2-morpholino-amino-3-methyl-butyronitrile 5.8 g of 4-aminomorpholine, 2.7 g of sodium cyanide and 10.7 g of 3-benzylthio-2-methylpropionaldehyde are reacted analogously to 7a). 16.1 g of 4-benzylthio-2-morpholinoamino-3-methylbutyronitrile are obtained, which are employed in the following step without further purification.

b)
4-(2-Benzylthio-1-methylethyl)-3-morpholinosydnone imine hydrochloride 16.0 g of the benzylthiobutyronitrile described under a) are reacted with 3.6 g of sodium nitrite in the presence of 4.3 ml of concentrated hydrochloric acid analogously to 7b). The crude product obtained after cyclization with hydrogen chloride is chromatographed on silica gel using dichloromethane/methanol (7:1). 2.0 g of 4-(2-benzylthio-1-methylethyl)-3-morpholinosydnone imine hydrochloride are obtained, which melt at 173° C. with decomposition after recrystallization from isopropanol/diethyl ether.

EXAMPLE 13

3-(2,6-Dimethylpiperidino)-4-phenoxymethylsydnone imine hydrochloride a)
2-(2,6-Dimethylpiperidino)amino-3-phenoxypropionitrile 12.8 g of 1-amino-2,6-dimethylpiperidine, 5.4 g of sodium cyanide and 15.0 g of phenoxyacetaldehyde are reacted analogously to 8a). 20.8 g of 2-(2,6-dimethylpiperidino)amino-3-phenoxypropionitrile are obtained, which are employed in the following step without further purification b)
3-(2,6-Dimethylpiperidino)-4-phenoxymethylsydnone imine hydrochloride 20.7 g of the phenoxypropionitrile described under a) are reacted with 5.2 g of sodium nitrite in the presence of 6.5 ml of concentrated hydrochloric acid analogously to 8b). The crude product obtained after cyclization with hydrogen chloride is chromatographed on silica gel using dichloromethane/methanol (9:1). 4.7 g of 3-(2,6-dimethylpiperidino)amino-4-phenoxymethylsydnone imine hydrochloride are obtained, which melt at 160°-161° C. with decomposition after recrystallization from isopropanol.

EXAMPLE 14

4-Benzyloxymethyl-3-(2,6 dimethylpiperidino)sydnone imine hydrochloride a)
3-Benzyloxy-2-((2,6-dimethylpiperidino)amino)propionitrile 12.8 g of 1-amino-2,6-dimethylpiperidine, 4.9 g of sodium cyanide and 15.0 g of benzyloxyacetaldehyde are reacted analogously to 8a). 23.3 g of 3-benzyloxy-2-((2,6-dimethylpiperidino)amino)propionitrile are obtained, which are employed in the following step without further purification.

b)
4-Benzyloxymethyl-3-(2,6-dimethylpiperidino)sydnone imine hydrochloride 23.0 g of the benzyloxypropionitrile described under a) are reacted with 5.5 g of sodium nitrite in the presence 6.9 ml of concentrated hydrochloric acid analogously to 8b). The crude product obtained after cyclization with hydrogen chloride is chromatographed on silica gel using dichloromethane/methanol (9:1). 4.0 g of 4-benzyloxymethyl-3-(2,6-dimethylpiperidino)sydnone imine hydrochloride are obtained as an oil.

EXAMPLE 15

4-Benzyloxymethyl-3-(2,6-dimethylpiperidino)-N-ethoxycarbonylsydnone imine 3.6 g of the 4-benzyloxymethyl-3-(2,6-dimethylpiperidino)sydnone imine hydrochloride described under 14) are reacted with 1.3 g of ethyl chloroformate in the presence of 1.8 g of sodium hydrogen carbonate analogously to 3). 2.8 g of 4-benzyloxymethyl-3-(2,6-dimethylpiperidino)-N-ethoxycarbonylsydnone imine are obtained, which melt at 56° to 57° C. after stirring with hexane.

Pharmaceutical preparations are described in the following

EXAMPLES A to F.

EXAMPLE A

Soft gelatin capsules, containing 5 mg of active compound per capsule:

|  | per capsule |
|---|---|
| Active compound | 5 mg |
| Triglyceride mixture fractionated from coconut oil | 150 mg |
| Capsule contents | 155 mg |

EXAMPLE B

Injection solution, containing 1 mg of active compound per ml:

|  | per ml |
|---|---|
| Active compound | 1.0 mg |
| Polyethylene glycol 400 | 0.3 ml |
| Sodium chloride | 2.7 mg |
| Water for injection purposes | to 1 ml |

EXAMPLE C

Emulsion, containing 3 mg of active compound per 5 ml

|  | per 100 ml of emulsion |
|---|---|
| Active compound | 0.06 g |
| Neutral oil | q.s. |
| Sodium carboxymethyl cellulose | 0.6 g |
| Polyoxyethylene stearate | q.s. |
| Glycerol, pure | 0.2 to 2.0 g |
| Flavouring | q.s. |
| Water (demineralized or distilled) | to 100 ml |

EXAMPLE D

Rectal medicament form, containing 4 mg of active compound per suppository

|  | per suppository |
|---|---|
| Active compound | 4 mg |
| Suppository base | to 2 g |

EXAMPLE E

Tablets, containing 2 mg of active compound per tablet

|  | per tablet |
|---|---|
| Active compound | 2 mg |
| Lactate (finely ground) | 2 mg |
| Maize starch (white) | 150 mg |
| Lactose | 60 mg |
| Microcrystalline cellulose | 50 mg |
| Polyvinylpyrrolidone | 20 mg |
| Magnesium stearate | 2 mg |
| Sodium carboxymethyl starch | 25 mg |
|  | 311 mg |

EXAMPLE F

Coated tablets, containing 1 mg of active compound per coated tablet

|  | per coated tablet |
|---|---|
| Active compound | 1 mg |
| Maize starch | 100 mg |
| Lactose | 60 mg |
| sec Calcium phosphate | 30 mg |
| Soluble starch | 3 mg |
| Magnesium stearate | 2 mg |
| Colloidal silica | 4 mg |
|  | 200 mg |

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. 3-Aminosydnone imines of the formula I

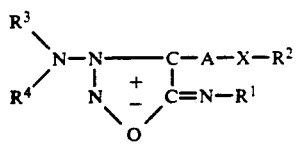

(I)

and their pharmacologically acceptable acid addition salts, in which

A denotes a straight-chain or branched alkylene chain having 1 to 6 C atoms;

X denotes one of the groups —O— or —S—;

$R^1$ denotes hydrogen or the radical —$COR^5$;

$R^2$ denotes an alkyl group having 1 to 6 C atoms; an alkenyl or alkynyl group in each case having 3 to 6 C atoms; a phenalkyl group having 1 to 4 C atoms in the alkyl group; a phenyl group; a phenyl group which is mono-, di- or trisubstituted by 1 to 3 halogen atoms and/or 1 to 3 alkyl radicals having 1 to 4 C atoms and/or 1 to 3 alkoxy radicals having 1 to 4 C atoms and/or 1 to 2 nitro groups and/or 1 to 3 hydroxyl groups and/or 1 to 3 alkylthio radicals having 1 to 4 C atoms and/or a trifluoromethyl radical; a phenylalkyl group having 1 to 4 C atoms in the alkyl group, the phenyl radical of which is mon-, di- or trisubstituted by 1 to 3 halogen atoms and/or 1 to 3 alkyl radicals having 1 to 4 C atoms and/or 1 to 3 alkoxy radicals having 1 to 4 C atoms and/or 1 to 2 nitro groups and/or 1 to 3 hydroxyl groups and/or 1 to 3 alkylthio radicals having 1 to 4 C atoms and/or a trifluormethyl radical;

$R^3$ and $R^4$, which may be identical or different, denote alkyl groups having 1 to 6 C atoms; alkenyl, alkynyl or cycloalkyl groups in each case having 3 to 6 C atoms; phenalkyl groups having 1 to 4 C atoms in the alkyl groups; phenyl groups; phenyl groups which are mono-, di- or trisubstituted by 1 to 3 halogen atoms and/or 1 to 3 alkyl radicals having 1 to 4 C atoms and/or 1 to 3 alkoxy radicals having 1 to 4 C atoms and/or 1 to 2 nitro groups and/or 1 to 3 hydroxyl groups and/or 1 to 3 alkylthio radicals having 1 to 4 C atoms and/or a trifluoromethyl radical;

phenalkyl groups having 1 to 4 C atoms in the alkyl group, the phenyl radical of which is mono-, di- or tri-substituted by 1 to 3 halogen atoms and/or 1 to 3 alkyl radicals having 1 to 4 C atoms and/or 1 to 3 alkoxy radicals having 1 to 4 C atoms and/or 1 to 3 alkylthio radical shaving 1 to 4 C atoms and/or a trifluormethyl radical; 1,1-dioxo-tetrahydrothiophene-3-yl, or $R^3$ and $R^4$, together with the nitrogen atom to which they are bonded, denote a heterocyclic ring of the formula

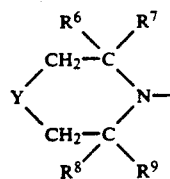

$R^5$ denotes an alkyl radical having 1 to 6 C atoms, which may also be substituted by alkoxy having 1 to 6 C atoms or by an alkylthio radical having up to 4 C atoms; a cycloalkyl radical having 5 to 7 C atoms; 2,6,6-trimethylbicyclo(3.1.1)heptan-3-yl; tricylco(3.3.1.1³·⁷)decan-1-yl; an alkoxy radical having 1 to 6 C atoms, which may also be substituted by alkoxy having 1 to 6 C atoms; a phenoxy radical; an alkoxycarbonyl radical having a total of 2 to 7 C atoms; a phenyl radical; a 1-naphthyl radical; a 2-naphthyl radical; a biphenylyl radical; a phenyl, 1-naphthyl, 2-naphthyl or biphenylyl radical which is mono-, di- or trisubstituted by 1 to 3 halogen atoms and/or 1 to 3 alkyl radicals having 1 to 4 C atoms and/or 1 to 3 alkoxy radical shaving 1 to 3 C atoms and/or 1 to 2 nitro groups and/or 1 or 2 hydroxyl groups and/or 1 or 2 alkylcarbonyloxy radials having 1 to 4 C atoms and/or 1 to 3 alkylthio radicals having 1 to 4 C atoms and/or trifluoromethyl radical and/or an imidazolyl radical; imidazolyl; pyridyl; thienyl; and styryl;

Y denotes one of the groups —$(CH_2)_n$—, —O—, —$S(O)_n$— or —$N(R^{10})$;

$R^6$, $R^7$, $R^8$, $R^9$ which may be identical or different, denote hydrogen or alkyl groups having 1 to 4 C atoms;

n denotes one of the numbers 0, 1 or 2;

$R^{10}$ denotes an alkyl radical having 1 to 4 C atoms, a phenyl radical or a radical of the formula —$COOR^{11}$, —COH, —$COR^{11}$ or —$S(O)_2R^{11}$; and $R^{11}$ denotes an alkyl radical having 1 to 4 C atoms.

2. Substituted 3-aminosydnone imines according to claim 1, characterized in that $R^3$ and $R^4$, together with the nitrogen atom to which they are bonded, denote a heterocyclic ring of the formula

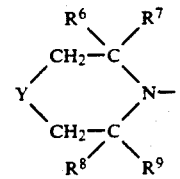

where Y preferably denotes one of the groups —$(CH_2)_o$—, —$(CH_2)_1$—, —O—, —S— or —$S(O)_2$—, and/or $R^6$, $R^7$, $R^8$ and $R^9$, which may be identical or different, denote hydrogen atoms or methyl groups, and/or $R^2$ denotes an alkyl radical having 1 to 6 C atoms, an alkenyl or alkynyl radical in each case having 3 to 5 C atoms, a phenalkyl radical having 1 to 3 C atoms in the alkyl group and an unsubstituted, mono-or disubstituted phenyl radical or an unsubstituted, mono- or disubstituted phenyl radical.

3. Substituted 3-aminosydnone imines according to claim 1, characterized in that $R^2$ denotes an alkyl radical having 1 to 4 C atoms, an alkenyl radical having 3 to 5 C atoms, a phenalkyl radical having 1 to 3 C atoms in the alkyl group or a phenyl radical.

4. Substituted 3-aminosydnone imines according to claim 1, characterized in that $R^2$ denotes ethyl, phenyl, benzyl or allyl, $R^3$ and $R^4$, together with the nitrogen atom to which they are bonded, denote morpholino or 2,6-dimethylpiperidino, $R^5$ denotes ethoxy, phenyl or methoxyphenyl and A denotes methylene or 1-methyl-ethylene.

5. 4-Benzylthiomethyl-3-(2,6-dimethylpiperidino)-sydnone imine and its pharmacologically acceptable acid addition salts.

6. 3-(2,6-Dimethylpiperidino)-4-phenoxymethylsydnone imine and its pharmacologically acceptable acid addition salts.

7. 4-Benzylthiomethyl-3-(2,6-dimethylpiperidino)-sydnone imine hydrochloride.

8. 3-(2,6-Dimethylpiperidino)-4-phenoxymethylsydnone imine hydrochloride.

9. Pharmaceutical composition, characterized in that it contains at least one substituted 3-aminosydnone imine of the general formula I according to claim 1 and/or a pharmacologically acceptable acid addition salt thereof as the active compound or active compounds together with pharmaceutically acceptable excipients and additives and, if appropriate, one or more other pharmacological active compounds.

10. A process for control or prophylaxis of disorders of the cardiovascular system, including angina pectoris, which comprises administering to a host in need thereof an effective amount of a compound of the general formula (I) according to claim 1 or a pharmacologically acceptable acid addition salt thereof.

* * * * *

UNITED STATES PATENT AND TRADEMARK OFFICE
CERTIFICATE OF CORRECTION

PATENT NO. : 5,079,244

DATED : January 7, 1992

INVENTOR(S) : Kujath et al.

It is certified that error appears in the above-identified patent and that said Letters Patent is hereby corrected as shown below:

On the title page, [75], surname of third inventor should read --Schonafinger--; same page, (56), name of first patentees should read --Bohn et al.--.

Title page, [75], surname of third inventor should read --Schonafinger--; same page, [56], name of first patentees should read --Bohn et al.--.

Col. 8, line 24, "(zolides)" should read --(azolides)--.

Col. 11, line 8, "A-CHO" should read --A'-CHO--.

Col. 11, line 49, "bound" should read --bound.--.

Col. 11, line 58, "preferred" should read --preferred.--.

Col. 12, line 28, "mixtures" should read --mixtures.--.

UNITED STATES PATENT AND TRADEMARK OFFICE
CERTIFICATE OF CORRECTION

PATENT NO. : 5,079,244

DATED : January 7, 1992

INVENTOR(S) : Kujath et al.

It is certified that error appears in the above-identified patent and that said Letters Patent is hereby corrected as shown below:

Col. 13, line 30, "05" should read --0.5--.

Col. 13, lines 64 to 68, insert a period "." midway between the IC value and $10^{-6}$.

Col. 14, line 4, insert a period "." midway between the IC value and $10^{-6}$; same col., line 5, insert a period "." midway between the IC value and $10^{-4}$.

Col. 16, line 54, "62" should read --6.2--.

Col. 21, line 27, "mon-" should read --mono--.

Col. 21, line 50 and Col. 22, line 10, "shaving" should read --having--.

Col. 22, line 1, "tricylco" should read --tricyclo--.

Col. 22, line 41, delete "preferably".

Signed and Sealed this

First Day of June, 1993

Attest:

MICHAEL K. KIRK

Attesting Officer

Acting Commissioner of Patents and Trademarks